United States Patent [19]

Franey et al.

[11] 4,279,773
[45] Jul. 21, 1981

[54] COMPOSITION USEFUL FOR DETECTING $H_2S$

[75] Inventors: John P. Franey, Bridgewater; Thomas E. Graedel, Mendham, both of N.J.

[73] Assignee: Bell Telephone Laboratories, Incorporated, Murray Hill, N.J.

[21] Appl. No.: 66,573

[22] Filed: Aug. 15, 1979

[51] Int. Cl.³ ............................................. G01N 31/22
[52] U.S. Cl. ..................................... 252/408; 422/87; 422/56
[58] Field of Search ..................... 422/56, 55, 83, 86, 422/87; 23/232 R; 252/408

[56] References Cited

U.S. PATENT DOCUMENTS

| | | | |
|---|---|---|---|
| 2,895,807 | 7/1959 | Sorg et al. | 23/232 R X |
| 3,607,093 | 9/1971 | Stone | 422/56 |
| 3,723,064 | 3/1973 | Liotta | 422/56 X |
| 3,985,017 | 10/1976 | Goldsmith | 23/232 R X |
| 4,019,865 | 4/1977 | Sinclair et al. | 422/86 |
| 4,168,146 | 9/1979 | Grubb et al. | 422/56 X |

FOREIGN PATENT DOCUMENTS 49-46276 12/1974 Japan ......................................... 422/56

OTHER PUBLICATIONS

Altieri, "Gas Analysis–1st Edition", American Gas Association, Inc. New York, 1945, p. 353.

*Primary Examiner*—Arnold Turk
*Attorney, Agent, or Firm*—Bruce S. Schneider

[57] ABSTRACT

An indicator device useful for detecting $H_2S$ is disclosed. This detector utilizes a polymer having a permeation constant of at least $5 \times 10^{-9}$ cm³ $H_2S$·cm thickness/(cm² area·sec·cm Hg) with an incorporated lead containing compound at concentration levels of at least 10 weight percent. These compositions are useful for detecting hydrogen sulfide in concentrations as low as approximately 10 parts per billion by volume, or concentrations of approximately 1 part per million in relatively short periods, e.g., five minutes, and are utilizable for quantitative measurements of $H_2S$ concentration.

5 Claims, 3 Drawing Figures

COMPOSITION USEFUL FOR DETECTING $H_2S$

BACKGROUND OF THE INVENTION

1. Field of the Invention

This invention relates to gas detection and, in particular, to the detection of sulfur containing gases.

2. Art Background

Employee exposure to hydrogen sulfide ($H_2S$) is a significant problem in many industrial environments. For example, cable vaults, particularly in southern regions of the United States, are subject to the presence of $H_2S$ evolved from the decomposition of vegetation. Alternatively, many industrial processes utilize $H_2S$ with an attendant possibility of employee exposure to this gas. Since $H_2S$ is extremely poisonous, e.g., approximately equal toxicity with hydrogen cyanide, the efficient and reliable detection of $H_2S$ is essential. Present methods for detecting $H_2S$ generally rely on the discoloration of a treated paper product. For example, paper is treated with a compound such as lead acetate. This compound forms black lead sulfide (PbS) when contacted with $H_2S$.

These paper based detectors have various disadvantages. Most significantly, the color change induced by $H_2S$ for most detectors is not stable and fades. (Certain mercury compounds do not fade but are extremely toxic.) Therefore, the use of detectors to indicate longer term low concentration exposure of employees to $H_2S$ is quite limited.

Because of the fading problem, the quantitative measurement of $H_2S$ concentration, especially at concentrations below a few parts per million, is particularly inconvenient since immediate measurement is required. Contact to $H_2S$ and immediate optical measurement exposes the optical instrument both to corrosion from outgassed $H_2S$ and to $H_2S$ from the environment. Prevention of this corrosion while maintaining acceptable accuracy from the measurement is generally excessively expensive. Additionally, the lead compounds used in commercial detectors present a health hazard. This hazard is significant since the compounds are not strongly adherent to the paper backings. Thus, careful handling and storage is required.

SUMMARY OF THE INVENTION

A sensitive means for detecting and quantitatively determining the presence of $H_2S$ has been found. This means involves dispersion of a suitable lead compound at concentration levels above 10 weight percent in a polymer having a permeation constant at 25 degrees C of at least $5 \times 10^{-9}$ cm$^3$ $H_2S$·cm thickness/(cm$^2$ area·sec·cm Hg). These polymeric bodies show discernible coloration at $H_2S$ levels as low as 10 parts per billion by volume. Optical measurements such as color spectrophotometry (*Color Difference of Opaque Materials, Instrumental Evaluation of,* ASTMD-2244, American Society of Testing and Materials, Philadelphia [1978]) are easily performable to yield quantitative measures of the $H_2S$ concentration to within 30% at the 10 parts per billion level and increasing to 10% at 1 part per million. Since the lead compound is contained in a polymeric body, there is no chemical hazard to the user.

DETAILED DESCRIPTION

Figure 1:
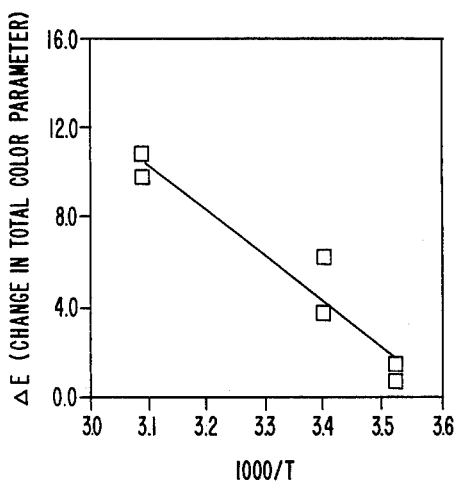
FIGS. 1, 2, and 3 represent quantitative results obtained by the subject invention in the detection of $H_2S$.

The inventive $H_2S$ detectors consist of a solid polymeric body having essentially two components-a polymer component and an additive that reacts with $H_2S$ to form a color change. As a pedagogic aid, each component is discussed separately.

1. THE ADDITIVE

Particularly advantageous compounds for use in the subject invention are lead containing compositions that react with HCl. The degree of reactivity of these compositions with HCl is quite important. If the reaction rate is insufficient, a corresponding insufficient sensitivity to $H_2S$ results. A method measuring the appropriate degree of reactivity is related to the stabilization of HCl evolution in polyvinylchloride by the additive. A method for determining the stabilization is described in W. H. Starnes, Jr. and I. M. Plitz, *Macromolecules,* 9, 633 (1976). Briefly, this determination is made by preparing a sample of polyvinylchloride having dispersed in the sample at least 10 weight percent of a lead compound additive. Approximately three-tenths of a gram of this polymeric sample is then inserted in a vessel having an exit tube. The vessel is immersed in a heat bath at 160 degrees C for five hours. The gases evolved from the polymer for five hours during heating are carried from the tube in an argon atmosphere and collected in solution. The amount of HCl thus collected is then measured by an ion-specific electrode. (It should be noted the stabilization of PVC is a convenient method for determining the appropriate degree of reactivity and does not at all imply the PVC is the only suitable polymer for use in the subject invention.)

Suitable additives and suitable levels of incorporation of these additives in the subject detectors are indicated by samples which allow a hydrogen chloride evolution no greater than $1 \times 10^{-5}$ moles/gr. of total sample when tested as described above. It is possible to use either a single additive or a combination of additives. Exemplary of a suitable additive is tribasic lead sulfate. This compound at concentration levels of 16 weight percent shows HCl evolution from polyvinylchloride (PVC) in a five hour period of $5 \times 10^{-6}$ moles/gr. Preferably, the compounds utilized should also be convenient. Thus although certain compounds which may satisfy the HCl evolution criteria are not precluded, their physical properties may make their employment generally unsatisfactory. For example, in the case of lead acetate, the material is a category I carcinogen (as rated by The Occupational Safety and Health Administration) and therefore is not desirable due to production hazards.

2. THE POLYMER

Although the reaction of $H_2S$ with the lead compounds discussed above is primarily a surface reaction, i.e., occurs with the additive compound which is found at or near the surface of the polymer, a certain minimum permeation of the polymer is required to achieve satisfactory color change. (For purposes of this disclosure, the word polymer includes blends of polymers.) Generally, the permeation constant to $H_2S$ should be greater than $5 \times 10^{-9}$ cm$^3$ $H_2S$·cm thickness/(cm$^2$ area·sec·cm Hg). If the permeability to $H_2S$ is less than this quantity, perceptible color changes within acceptable time periods, i.e., periods less than five minutes at 1 part per million $H_2S$ are generally not achievable.

A polymer is also advantageously chosen so that the contrast between its virgin state and its color upon exposure to $H_2S$ is significant. Typically, polymers showing a white color are preferably utilized. In this manner, the contrast between the white polymer color and the black color typically developed upon exposure to $H_2S$ is quite high. Additionally, it is possible to incorporate additives such as titanium dioxide into the polymer to change the inherent color of the polymer and provide a greater contrast. Similarly, it is possible to include in the polymer other additives, such as plasticizers, which do not react with $H_2S$, but yield desirable manufacturing properties. Obviously, the polymer must be chosen so that it does not substantially reduce the reactivity of the lead additive to $H_2S$.

3. FORMATION OF THE SUBJECT DETECTORS

The additive and polymer are chosen so that the additive is dispersed in the polymer. That is, the additive should essentially homogeneously be dispersed in the polymer. Concentration gradients of additive in the polymer which degrade uniformity between detectors made in one lot generally are not acceptable since quantitative measure is significantly affected. Generally it is desirable to maintain uniformity so that samples from the same lot do not exhibit color changes which vary more than $\frac{1}{2}$ color unit (ASTMD-2244 test) between samples in the same lot. However, if quantitative measure is not desired, larger gradients are tolerable. The additive advantageously is incorporated in the polymer by introducing the additive into the monomer mixture before polymerization. This technique is commonly utilized for additives such as colorants and is adequately described in *The PVC Encyclopedia,* at page 756, L. I. Ness, Ed., Marcel Dekker, New York, (1976).

The weight percent of lead additive compound to polymer must be greater than 10 weight percent. If lower ratios are used, inadequate color changes are obtained in acceptable time periods. It should be noted that this degree of additive in the polymer somewhat degrades mechanical properties. Therefore, generally, it is inadvisable to increase the additive ratio of additive to polymer beyond 20 weight percent. However, if mechanical strength is not essential higher concentrations are not precluded. Since, as described previously, the reaction is primarily a surface reaction, the shape of the detector is not in any way critical. Convenient dispensing and storage results when a disk-like form having a diameter in the range 1 to 2 inches and a thickness in the range 0.125 to 0.250 inch is employed.

As discussed previously, quantitative measurements of $H_2S$ concentrations are possible. These measurements are made by comparing the optical properties as measured by the ASTMD-2244 test with that measured for a controlled sample. For example, a polymer having the desired lead additive in an appropriate concentration is exposed to a known quantity of $H_2S$ (precise control of $H_2S$ concentration has been fully disclosed in J. P. Franey, *Journal of the Electrochemical Society,* 78-2, 659 (1978)). The ASTMD test is then performed on this sample and a number of other samples of identical composition exposed to different levels of $H_2S$ concentrations. A graph of $H_2S$ concentration vs. measured color unit is then established. Samples having the same composition used to detect $H_2S$ are measured by the ASTMD test and compared with the standard graph to determine the concentration.

Figure 2:
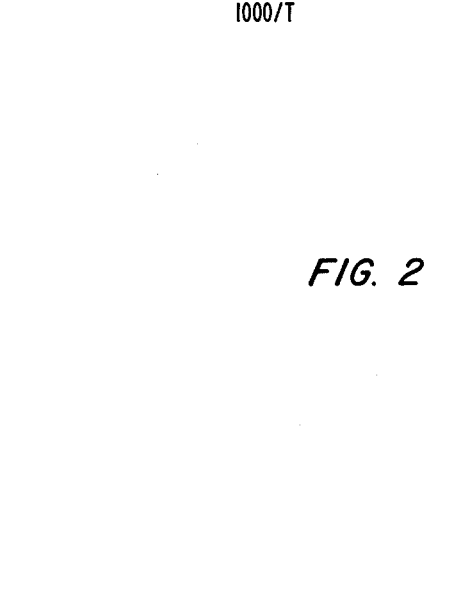
Figure 3:
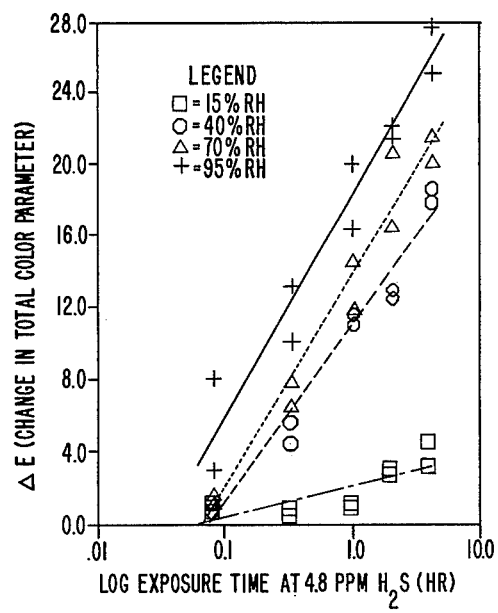
Figure 3:
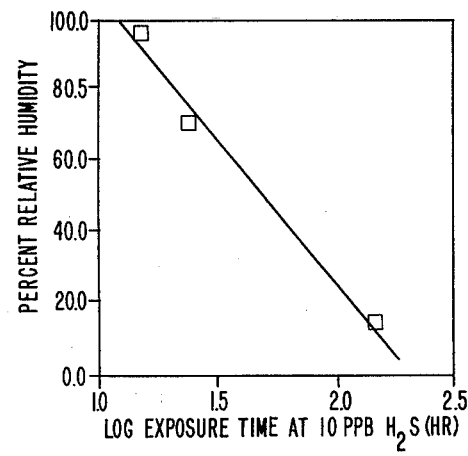

It should be noted that humidity and temperature effect the results obtained in the ASTMD test. As shown in FIGS. 1 and 2, temperature and humidity respectively can have a significant effect. Therefore, the standard graph should be compiled under humidity and temperature conditions similar to those utilized in actual measurement. FIG. 3 shows the minimum exposure time as a function of relative humidity when concentrations were measured in the parts per billion range. As can be seen, longer exposure times are necessary at lower humidities. Concentrations in this range are detectable and are useful to insure that excessive cumulative exposure to $H_2S$ is avoided.

Although quantitative measurements are often desirable, a qualitative measure of the $H_2S$ concentration is obtainable by preparing a color shade chart. This chart is prepared in an equivalent manner to the standard graph in the quantitative samples, i.e., by exposing the sample to various concentration levels and noting the color obtained. The compilation of these colors at various concentrations give a comparison chart to determine approximate concentration ranges. It is possible for convenience to include such charts with the detectors so that approximate concentration levels are measurable in the field.

We claim:

1. A detection apparatus suitable for quantitatively detecting $H_2S$ comprising a polymer having incorporated a lead containing additive characterized in that said lead containing additive reacts with $H_2S$, and is present in a quantity of at least 10 weight percent of said polymer wherein said quantity is a quantity which would be sufficient to avoid more than $1 \times 10^{-5}$ moles of HCl evolution in five hours for each gram of a PVC sample utilizing said additive in said quantity, and wherein the permeation constant at 25 degrees C. of said polymer is at least $5 \times 10^{-9}$ cm$^3$ $H_2S$·cm thickness/(cm$^2$ area·sec·cm Hg).

2. The detection apparatus of claim 1 wherein said lead containing additive is tribasic lead sulfate.

3. The detection apparatus of claim 2 wherein said polymer is polyvinylchloride.

4. The detection apparatus of claim 1 wherein said polymer is polyvinylchloride.

5. The detection apparatus of claim 1 wherein said weight percent is in the range 10 to 20 percent.

* * * * *